United States Patent [19]

Callander

[11] 4,072,677
[45] Feb. 7, 1978

[54] PENICILLIN SYNTHESIS
[75] Inventor: Sidney Edward Callander, Worthing, England
[73] Assignee: Beecham Group Limited, United Kingdom
[21] Appl. No.: 746,137
[22] Filed: Nov. 30, 1976
[30] Foreign Application Priority Data
Dec. 13, 1975 United Kingdom ............... 51136/75
[51] Int. Cl.$^2$ ................... C07D 499/68; C07D 499/70
[52] U.S. Cl. ............................ 260/239.1; 260/306.7 C
[58] Field of Search ....................... 260/239.1, 306.7 C
[56] References Cited
U.S. PATENT DOCUMENTS
3,860,579   1/1975   Ferres et al. ...................... 260/239.1

OTHER PUBLICATIONS

Hennis et al., I and E. C. Product Research and Development, 7(2), 96–101, (1968).

Primary Examiner—Gerald A. Schwartz
Attorney, Agent, or Firm—Jacobs & Jacobs

[57] ABSTRACT

Process of preparing phthalidyl ampicillin or other orally absorbable penicillin ester by esterification of the parent penicillin in a two-phase system using a phase transfer catalyst which increases the solubility of a salt form of the penicillin in the water-immiscible solvent used in the process. The phase transfer catalysts are quaternary ammonium salts or tertiary amines of non-low molecular weight, or crown ethers.

10 Claims, No Drawings

PENICILLIN SYNTHESIS

This invention relates to a process for preparing certain orally absorbable penicillin esters.

More specifically, this invention relates to the preparation of certain orally absorbable penicillin esters by the esterification of the parent penicillin in the presence of a phase transfer catalyst.

Reactions between simple organic acid salts and alkyl halides in the presence of quaternary ammonium salts or tertiary amines as catalysts to give the corresponding acid-alkyl esters are known, for example Hennis et al: I and E.C. Product Research and Development 7 (2) 96–101 (1968). In this paper, for example, sodium acetate was reacted with benzyl chloride in an organic solvent in the presence of different tertiary amines as catalysts, and satisfactory yields of benzyl acetate were obtained in several cases. Also sodium benzoate was reacted with n-butyl chloride in an organic solvent in the presence of triethylamine and an alkyl iodide, or in the presence of the corresponding pre-formed quaternary salt, as catalyst, and satisfactory yield of n-butyl benzoate were again obtained in several cases.

The phthalidyl ester of 6-[D-α-aminophenylacetamido] penicillanic acid, hereinafter referred to as ampicillin phthalidyl ester, of formula (A) below:

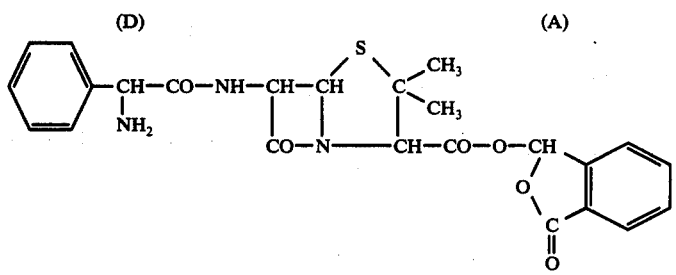

is disclosed in UK Pat. No. 1364672. This penicillin ester produces high serum concentrations of the parent penicillin, namely 6-[D,α-aminophenylacetamido]-penicillanic acid, hereinafter referred to as ampicillin, when administered orally. One of the processes for the preparation of this compound disclosed in the Patent comprises reacting a compound of formula (B):

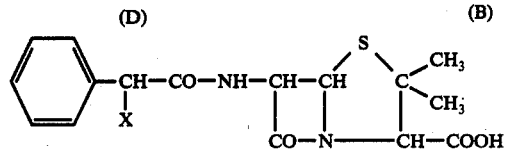

or a reactive esterifying derivative thereof, in which formula X is an amino group, a protected amino group, or a group convertible to an amino group, with a compound of formula (C):

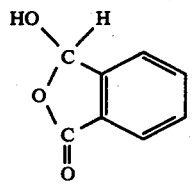

or a reactive esterifying derivative thereof, and if X is not an amino group, subsequently converting it to an amino group under neutral or acid conditions.

It has now been discovered that the phthalidyl ester of ampicillin and certain other penicillin esters may be prepared by esterification of the parent penicillin in a two phase system using a phase transfer catalyst. Such reactions can give good yields of the ester product. Also, when the esterification is to be carried out on a large scale, the use of this reaction technique can give advantages over conventional esterification techniques in terms of reduced mechanical problems associated herewith.

It is believed that the use of phase transfer catalyst in the preparation of penicillin esters has not been reported in the literature.

Accordingly, the present invention provides a process for the preparation of a compound of the formula (I):

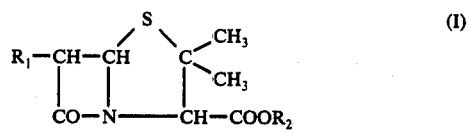

wherein $R_1$ is a group $R_3$— *$CH(R_4)$—CO—NH—, or a group $R_5R_6C=N$—, wherein $R_3$ is phenyl, p-hydroxyphenyl, cyclohexadienyl, or 2- or 3-thienyl, $R_4$ is an amino or protected amino group, $R_5$ and $R_6$ are both methyl or together with the carbon atom to which they are joined represent a cycloheptyl ring; and $R_2$ is a group of formula (II) or IIA):

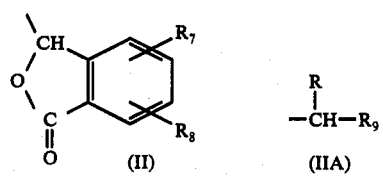

wherein $R_7$ and $R_8$ are the same or different and are hyrogen, methyl or methoxy, $R_9$ is acetoxy, pivaloyloxy or ethoxycarbonyloxy, and R is hydrogen or methyl; which process comprises reacting an aqueous solution of a compound of the formula (III):

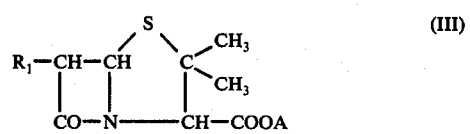

wherein $R_1$ is as defined in formula (I) and A is a salt forming ion, with a solution in a water-immiscible organic solvent of a compound R₂OH, wherein R₂ is as defined in formula (I), or a reactive esterifying derivative thereof, in the pesence of a phase transfer catalyst.

In the aforesaid process, when R₁ contains a protected amino group R₄, the process is normally followed by the optional step of deprotecting that amino group to give the corresponding α-aminopenicillin ester. It will be realised that when this deprotection step is carried out by acid hydrolysis, an acid addition salt of the desired α-aminopenicillin ester will be formed.

The carbon atom marked * in R₁ is in the D configuration.

By the term 'phase transfer catalyst' used herein is meant a compound which increases the solubility of a compound of the formula (III) in the water-immiscible solvent used in the process of the invention.

R₁ may contain a protected amino group R₄. Examples of suitable protected amino groups R₄ include the benzyloxycarbonylamino (R₄ = NH CO₂CH₂Ph) or substituted benzyloxycarbonylamino groups which are convertible to amino by catalytic hydrogenation; and various groups which regenerate the amino group on mild hydrolysis.

Examples of protected amino groups which may subsequently be converted to NH₂ by mild acid hydrolysis include enamine groups of general formula (IV) or tautomeric modifications thereof:

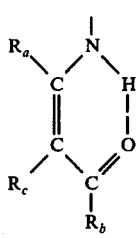
(IV)

wherein R_a is an alkyl, aralkyl or aryl group, R_b is alkyl, aralkyl, aryl, alkoxy, aralkoxy, or amino group and R_c is a hydrogen atom or an alkyl, aralkyl or aryl group or R_c together with either R_a or R_b completes a carbocyclic ring. Preferably R₄ is a (1-methoxycarbonylpropen-2-yl)amino group, i.e. a group (IV) wherein R_a is methyl, R_c is hydrogen and R_b is methoxy.

Another example of a group R₄ which can be converted to NH₂ after the esterification reaction is the azido group. In this case, the final conversion into NH₂ may be brought about by either catalytic hydrogenation or electrolytic reduction.

The actual choice of protected amino group R₄ for use in the process will of course be influenced by the nature of the penicillin ester being formed. For example, when the ester grouping R₂ is a phthalidyl type group of formula (II) then the protected amino group must not be one that requires alkaline hydrolysis to convert it to amino, since hydrolysis of this ester grouping occurs under such conditions. Again with the phthalidyl ester grouping, if hydrogenation is required to convert a protected amino group to amino, for example in the case of the benzyloxycarbonylamino protected amino group, then care must be taken to avoid substantial decomposition of the ester grouping during this hydrogenation. It has been found that for the phthalidyl type ester grouping a particularly suitable protected amino group R₄ is the (1-methoxycarbonylpropen-2-yl) amino group.

When R₂ is a group of formula (II) as hereinbefore defined, it is most suitably a phthalidyl group, or a 5,6-dimethoxyphthalidyl group. Examples of suitable R₂ groups of formula R₉—CH(R)— as hereinbefore defined include the following groups: acetoxymethyl, α-acetoxyethyl, pivaloyloxymethyl, α-pivaloyloxyethyl, ethoxycarbonyloxymethyl and α-ethoxycarbonyloxyethyl.

In the compound of formula (III), which is used as a starting material in the process of the invention, A is a salt forming ion. The most suitable ions A are alkali and alkaline earth metal ions such as the sodium and potassium ions, and generally the preferred ion A is the sodium ion.

The compound of formula (III) is reacted with a compound R₂OH or a reactive esterifying derivative thereof. By the term 'reactive esterifying derivative' when used herein is meant a derivative which when reacted with a compound of the formula (III) takes part in a condensation reaction with the formation of an ester linkage. Examples of such R₂OH derivatives include groups R₂X wherein X is a group readily displaceable by a nucleophile, such as an alkylsulphonyloxy group, an arylsulphonyloxy group or a halogen atom. Often X will simply be a halogen atom such as bromine or iodine.

Examples of phase transfer catalyst which have been found to be of particular use in the process of the invention are quaternary ammonium salts, tertiary amines, and crown ethers. However, as will become apparent, certain low molecular weight quaternary ammonium salts and tertiary amines cannot be used as catalysts.

When the phase transfer catalyst is a quaternary ammonium salt, then suitable catalysts include those of formula (V):

(V)

wherein Y⁻ is an anion, R₁₀ and R₁₁ are C₁₋₁₈ organic groups, R₁₂ is a C₁₋₁₀ alkyl group, R₁₃ is a C₁₋₆ alkyl group, R₁₁, R₁₂ and R₁₃ and the nitrogen to which they are attached can form pyridine, and R₁₀R₁₁R₁₂R₁₃N⁺ contains at least nine carbon atoms.

Suitable examples of the groups R₁₀ and R₁₁ which are C₁₋₁₈ organic groups are C₁₋₁₈ straight chain alkyl groups, and, more generally, C₁₋₁₈ hydrocarbon groups which may contain one or more hetero atoms and which are joined to nitrogen through saturated carbon atoms. Often R₁₀ will be a C₁₋₁₈ organic group as described and R₁₁ will be a C₁₋₁₀ straight chain alkyl group.

The anion Y will normally be a halide such as a chloride or bromide, preferably a bromide, as quaternary ammonium salts are conventionally prepared by heating a tertiary amine with an organic halide. However other conventional anions such as those formed from inorganic acids can be used if desired, provided that they are inert under the chosen reaction conditions.

Suitable compounds of formula (V) are those derived from the cations: tetrabutylammonium, tetrapropylammonium, tributylammonium and trioctylmethylammonium.

It has been found that a particularly suitable quaternary ammonium salt catalyst is tetrabutylammonium bromide. Cetyl pyridinium bromide may also be used with advantage in the process of the invention.

The phase transfer catalysts may also be a tertiary amine, in which case suitable catalysts include amines of the formula $R_{14}R_{15}R_{16}N$, wherein the R groups are each $C_{1-12}$ alkyl groups and the amine must contain at least 7 carbon atoms. Preferably at least $R_{14}$ and $R_{15}$ are $C_{3-10}$ straight chain alkyl groups.

A particularly useful tertiary amine phase transfer catalyst is dioctylmethylamine.

Crown ethers have also been found to be useful phase transfer catalysts. Examples of suitable crown ethers include dibenzo-18-crown-6, and dicyclohexyl-18-crown-6.

The compounds of the formula (III) are readily soluble in aqueous solution, and indeed are often prepared in this form. The compounds $R_2OH$, or reactive esterifying derivatives thereof, are readily soluble in water-immiscible solvents. One advantage of the use of a phase transfer catalyst is that the two process reactants can be reacted together in these different solvent systems. The catalyst acts to increase the solubility of the compound of the formula (III) in the water-immiscible solvent where it can react with the $R_2OH$ compound to form the (amino protected) ester. This ester is itself readily soluble in the water-immiscible solvent, so that on completion of the process it may readily be separated from the aqueous phase.

In the process the concentration of a compound of the formula (III) in the aqueous solvent is suitably in the range 5 to 25% w/v, with 20 to 25% being particularly suitable. One of the advantages of the process of the invention is that such relatively dilute aqueous concentrations may be used.

Suitable water-immiscible organic solvents include those in which both the esterifying agent $R_2OH$ and the reaction product of the formula (I) are reasonably soluble, and thus include chlorinated hydrocarbon solvents such as methylene dichloride and chloroform; common ester solvents such as ethyl acetate and isopropyl acetate; and methyl isobutyl ketone.

The concentration of the esterifying agent in the organic solvent is suitably in the range 5 to 25% w/v, preferably about 10%. Generally, the concentration must not be so high that the resultant solution is too viscous too be readily stirred.

The concentration of the phase transfer catalyst in the reaction medium will often be in the range 0.05 to 0.5 molar ratio with respect to the compound of the formula (III), preferably 0.1 to 0.2 molar ratio. Generally it has been found that if the catalyst concentration is substantially higher than 0.5 molar ratio as defined then some of the catalyst tends to be carried through into the product. Similarly, if the catalyst concentration is substantially lower than 0.05 molar ratio as defined then the reaction rate will often be unacceptably slow at temperatures suitable for penicillin synthesis.

The process will normally be carried out at a temperature in the range 10° to 35° C. Such a range allows a reasonable rate of reaction whilst limiting the temperature dependent decomposition of the penicillin. Under such conditions the reaction time is normally between 2 to 10 hours. Preferably the temperature is 20° to 25° C. At such temperatures the reaction time is often about 5 to 6 hours.

After the phase transfer reaction is completed, the organic phase containing the (amino protected) ester is normally separated from the aqueous phase, and the protected amino group, if present, then deprotected in conventional manner. It will be realised of course that if this deprotection is carried out by acid hydrolysis then the resultant amino group will be present as an acid addition salt, and the penicillin ester product may be isolated as such. The most suitable acid addition salt is the hydrochloride, but salts with other organic and inorganic acids may be formed in the usual way.

The desired penicillin ester, or acid addition salt thereof when appropriate, is then isolated from the organic phase in the usual manner.

The phthalidyl ester of ampicillin is one particularly preferred ester that can be prepared by means of the process of the invention.

Thus in one preferred embodiment, the present invention provides a process for the preparation of the phthalidyl ester of [D-N-(1-methoxycarbonylpropen-2-yl)-α-aminophenylacetamido] penicillanic acid, which process comprises reacting an aqueous solution of a salt of [D-N-(1-methoxycarbonylpropen-2-yl)-α-aminophenylacetamido]penicillanic acid with a solution of bromophthalide in a water-immiscible organic solvent, in the presence of a phase transfer catalyst.

The phthalidyl ester of ampicillin may be isolated from the N-protected ester formed in the organic phase of the above process in the usual manner, for example as the acid addition salt after mild acid hydrolysis to remove the amino protecting group.

The salt of the penicillanic acid used in the process is suitably the sodium salt.

The compounds of the formula (III), and the compounds $R_2OH$ and reactive esterifying derivatives thereof are well known in the art and may be made by any of the known methods.

Quaternary ammonium salt and tertiary amine phase transfer catalysts may simply be prepared by the conventional techniques used for quaternary ammonium salt and tertiary amine synthesis.

Crown ether phase transfer catalysts may be prepared for example as described in C. J. Pedersen, J. Amer. Chem. Soc. 89, 7017 (1967). The two specific crown ethers mentioned in this specification are commercially available from the Aldrich Chemical Co. Inc.

In a further embodiment, the invention provides a compound of the formula (I) as defined, whenever prepared by the process of the invention.

When $R_1$ in a compound of the formula (I) prepared in this manner is $R_3C^*H(R_4)CONH-$ as defined (in which $R_4$ is protected amino), the compound of the formula (I) will normally be converted thereafter into the corresponding compound of the formula (I) wherein $R_4$ is amino. The invention therefore also provides such '$R_4$ amino' compounds of the formula (I) whenever prepared in this manner.

The following Examples illustrate the invention:

EXAMPLE 1 i. Preparation of sodium - [D-N-(1-methoxycarbonyl propen-2-yl)-α-aminophenylacetamido]penicillanate A slurry of 6-aminopenicillanic acid (21.6g, 0.1M) in water (60 ml) cooled to 5° C was treated with 10% sodium hydroxide solution to give a clear solution at pH 7.8. Acetone (85 ml) was added and the solution was cooled to −18° C.

At the same time a mixed anhydride was being prepared by adding sodium D-N-(1-methoxycarbonyl-propen-2-yl)-α-aminophenylacetate (27.1g) to a mixture of ethylchloroformate (10.0 ml) and diaminopropanol (0.2 ml) in acetone (170 ml) at −35° C. After ca. 15 minutes this was added to the 6-aminopenicillanic acid solution. After ca. 15 minutes, the solution, now containing sodium-[D-N-(1-methoxycarbonyl propen-2-yl)-α-aminophenylacetamido]penicillanate, was partially concentrated under reduced pressure to remove most of the acetone.

ii. Esterification of the product of (i)

To the solution of sodium-[D-N-(1-methoxycarbonyl propen-2-yl)-α-aminophenylacetamido]penicillanate was added methylene dichloride (200 ml), sodium bicarbonate (20g), sodium chloride (30g), tetrabutylammonium bromide (6g) and bromophthalide (34g) in methylene dichloride (100 ml).

The reaction mixture was stirred for ca. 5 hours at 20°–25° C, water (100 ml) was added and the lower methylene dichloride phase isolated. This was washed with 2% aqueous sodium bicarbonate, and contained the N-protected ampicillin phthalidyl ester.

iii. Hydrolysis of the product of (ii)

To the MDC solution, containing the N-protected ampicillin phthalidyl ester was added water (400 ml) heptane (300 ml) and 18% hydrochloric acid (30 ml) at ca. 10° C. After 1.5 hours the lower aqueous phase was isolated and washed with a 1:1 mixture of methylene dichloride and heptane (400 ml).

iv. Extraction of the Phthalidyl Ester of Ampicillin (as the hydrochloride)

To the aqueous solution was added methylene dichloride (400 ml) and sodium chloride (40g), with stirring. The methylene dichloride solution was isolated, washed with dilute sodium chloride solution and dried over magnesium sulphate.

The product, *ampicillin phthalidyl ester hydrochloride*, was precipitated by the addition of heptane (400 ml) filtered, washed with heptane, and dried at 50° C.

| Yield | : | 40.2g |
| Assay (HPLC) | : | 94.9% |
| Yield from 6-APA | : | 74% |

EXAMPLE 2

Several variations on the procedure of Example 1 were carried out, and in some cases the product was not isolated, but the yield was determined by measurement of optical rotation of the methylene dichloride solution. Other quaternary salts were examined:

| Salt | Yield of Ampicillin Phthalidyl Ester hydrochloride |
|---|---|
| Cetyl trimethylammonium bromide | ca. 60% |
| Cetyl pyridinium bromide | 60 – 70% |
| Phthalidyl triethylammonium bromide | ca. 25% |
| Phthalidyl tripropylammonium bromide | ca. 38% |
| Phthalidyl tributylammonium bromide | ca. 45% |

EXAMPLE 3

The procedure for Example 1 was repeated, except that the following tertiary amines or their hydrochlorides were used in the place of the quaternary ammonium salts. Triethylamine was also used in place of sodium hydroxide for dissolution of the 6-APA. The following results were obtained:

| Amine | Yield |
|---|---|
| Tripropylamine | 35% |
| Tributylamine | 37% |
| Dioctylmethylamine | 60% |
| Trioctylamine | 45% |

As in Example 1, about 0.02 moles (i.e. 0.2 molar equivalents) of the catalyst was used.

EXAMPLE 4

The procedure of Example 1 was repeated, but dicyclohexyl-18-crown-6 (6g, ca. 0.02 moles) replaced tetrabutylammonium bromide. The yield of ampicillin phthalidyl ester hydrochloride was 60%.

EXAMPLE 5

The procedure of Example 1 was repeated, replacing the tetrabutylammonium bromide by the following quaternary ammonium salts and the yields of ampicillin phthalidyl ester hydrochloride are as follows:

| Salt | Yield of Ester |
|---|---|
| Tributylethylammonium ethosulphate | 75% |
| Tetrapropylammonium bromide | 70% |
| Trioctylmethylammonium bromide | 70% |

What we claim is:

1. A process for the preparation of a compound of formula (I):

$$\underset{O}{R_1} \underset{\diagup}{\overset{\diagdown}{\phantom{X}}} \overset{S}{\underset{N}{\phantom{X}}} \overset{CH_3}{\underset{CO_2R_2}{\phantom{X}}} \quad (I)$$

wherein $R_1$ is a group $$R_3-\overset{*}{\underset{R_4}{C}H}-CO-NH-$$

or $$\underset{R_6}{\overset{R_5}{\diagdown}}C=N-,$$

wherein $R_3$ is phenyl, p-hydroxyphenyl, cyclohexadienyl, or 2-or 3-thienyl, $R_4$ is an amino or *conventional penicillin* protected amino group, $R_5$ and $R_6$ are both methyl or, together with the carbon atom to which they are joined, represent a cycloheptyl ring; and $R_2$ is a group of formula (II) or (IIA):

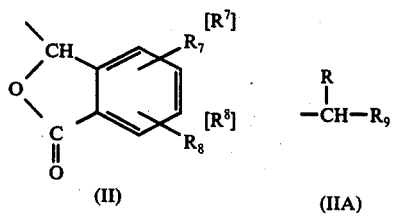

(II)   (IIA)

wherein $R_7$ and $R_8$ are the same or different and are hydrogen, methyl or methoxy, $R_9$ is acetoxy, pivaloyloxy or ethoxycarbonyloxy, and R is hydrogen or methyl;

which process comprises reacting an aqueous solution of a compound of formula (III):

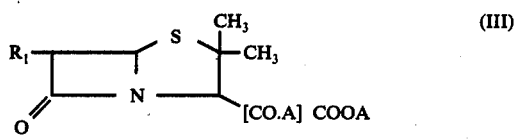

wherein $R_1$ has the above meaning and A is a salt-forming ion, with a solution in a water-immiscible organic solvent of a compound $R_2OH$ or a reactive esterifying derivative thereof, in the presence of a phase transfer catalyst which is a compound which increases the solubility of the salt form of the parent penicillin in the water-immiscible solvent.

2. A process as claimed in claim 1 wherein $R_3$ is phenyl.

3. A process as claimed in claim 1 wherein $R_2$ is a group of formula (II) wherein $R^7$ and $R^8$ are both hydrogen.

4. A process as claimed in claim 1 wherein the phase transfer catalyst is a quaternary ammonium salt, a tertiary amine or a crown ether.

5. A process as claimed in claim 4 wherein the phase transfer catalyst is a compound of formula (V):

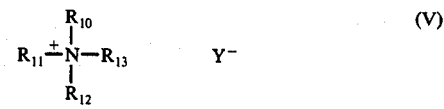

wherein $Y^-$ is an anion, $R_{10}$ and $R_{11}$ are $C_1$-$C_{18}$ organic groups, $R_{12}$ is a $C_1$-$C_{10}$ alkyl group, $R_{13}$ is a $C_{1-6}$ alkyl group, or $R_{11}$, $R_{12}$ and $R_{13}$ and the nitrogen to which they are attached may form a pyridine ring, the moiety $R_{10}R_{11}R_{12}R_{13}N^+$ containing at least nine carbon atoms.

6. A process as claimed in claim 5 wherein $R_{10}$ and $R_{11}$ are $C_1$-$C_{10}$ straight chain alkyl groups.

7. A process as claimed in claim 6 wherein the phase transfer catalyst is a compound in which the cation is selected from:
tetrabutylammonium;
tetrapropylammonium;
tributylethylammonium;
trioctylmethylammonium.

8. A process for the preparation of the phthalidyl ester of [D-N-(1-methoxycarbonylpropen-2-yl)-α-aminophenylacetamido]penicillanic acid, which process comprises reacting an aqueous solution of a salt of [D-N-(1-methoxycarbonylpropen-2-yl)-α-aminophenylacetamido]penicillanic acid with a solution of bromophthalide in a water-immiscible organic solvent, in the presence of a phase transfer catalyst.

9. A process as claimed in claim 8 which further comprises hydrolysis of the resulting phthalidyl ester of [D-N-(1-methoxycarbonylpropen-2-yl)-α-aminophenylacetamido]penicillanic acid to give phthalidyl ampicillin or an acid addition salt thereof.

10. A process for the preparation of a penicillin ester by esterification of the parent penicillin having an unesterified carboxyl group in the 3-position in a two-phase system using a phase transfer catalyst which process comprises reacting an aqueous solution of the parent penicillin in which the carboxyl group in the 3-position is in salt form with the hydrogen atom of the carboxyl group replaced by a salt forming ion with a compound $R_2OH$ dissolved in a water-immiscible solvent in the presence of a phase transfer catalyst which is a compound which increases the solubility of the salt form of the parent penicillin in the water-immiscible solvent, $R_2$ in the compound $R_2OH$ having the meaning defined in claim 1.

* * * * *